United States Patent [19]
Drbal

[11] Patent Number: 4,739,645
[45] Date of Patent: Apr. 26, 1988

[54] APPARATUS FOR CALIBRATING A SENSOR FOR DETECTING THE PRESENCE OF A GAS IN A LIQUID

[75] Inventor: Vladimir J. Drbal, Belmont, Calif.
[73] Assignee: Kelsius Inc., San Carlos, Calif.
[21] Appl. No.: 920,512
[22] Filed: Oct. 17, 1986
[51] Int. Cl.[4] .......................................... G01N 33/00
[52] U.S. Cl. ............................................... 73/1 G
[58] Field of Search .................. 73/1 G, 1 R; 422/58, 422/59; 436/11

[56] References Cited

U.S. PATENT DOCUMENTS

| | | | |
|---|---|---|---|
| 3,824,157 | 7/1974 | Macur | 73/1 G |
| 3,962,046 | 6/1976 | Morrison | 736/1 G |
| 3,973,915 | 8/1976 | Raffacle et al. | 23/259 |
| 4,057,499 | 11/1977 | Buono | 210/136 |
| 4,221,567 | 9/1980 | Clark et al. | 23/230 |
| 4,251,483 | 2/1981 | Carroll | 422/68 |
| 4,253,845 | 3/1981 | Smernoff | 436/11 |
| 4,256,461 | 3/1981 | Wallace et al. | 23/230 B |
| 4,266,941 | 5/1981 | Sullivan | 73/1 G |
| 4,301,117 | 11/1981 | Smernoff | 422/99 |
| 4,567,748 | 2/1986 | Klass et al. | 73/1 G |

FOREIGN PATENT DOCUMENTS 3213241 10/1983 Fed. Rep. of Germany ....... 73/1 G

*Primary Examiner*—Stewart J. Levy
*Assistant Examiner*—Robert R. Raevis
*Attorney, Agent, or Firm*—Ciotti, Murashige, Irell & Manella

[57] ABSTRACT

A calibration vial is described for storing and calibrating under sterile conditions a blood gas sensor that comprises an optical fiber whose sensing end carries a sensing element, such as a chromophore or fluorophore. The vial contains a calibrating liquid and, in its preferred embodiment, is structured to keep the end of the filter wet and permit fast calibration of the sensor without spillage of the calibrating liquid. The vial has a tubular inner calibration chamber in which the end of the fiber resides and which has a sterile filter-plugged gas inlet in its bottom and an outer concentric calibrating liquid reservoir chamber. The bottoms of the two chambers are interconnected by one or more liquid reflux ports that are positioned such that the gas coming into the bottom of the calibration chamber aspirates liquid from the reservoir chamber into the calibration chamber. This permits rapid mixing and circulation of the liquid upwardly through the calibration chamber. The upper ends of the chambers are interconnected by a passageway through which liquid is returned to the reservoir and spent gas exits the calibration chamber. The spent gas is vented to the atmosphere via a vent that opens into the top of the reservoir chamber above the liquid level therein.

27 Claims, 4 Drawing Sheets

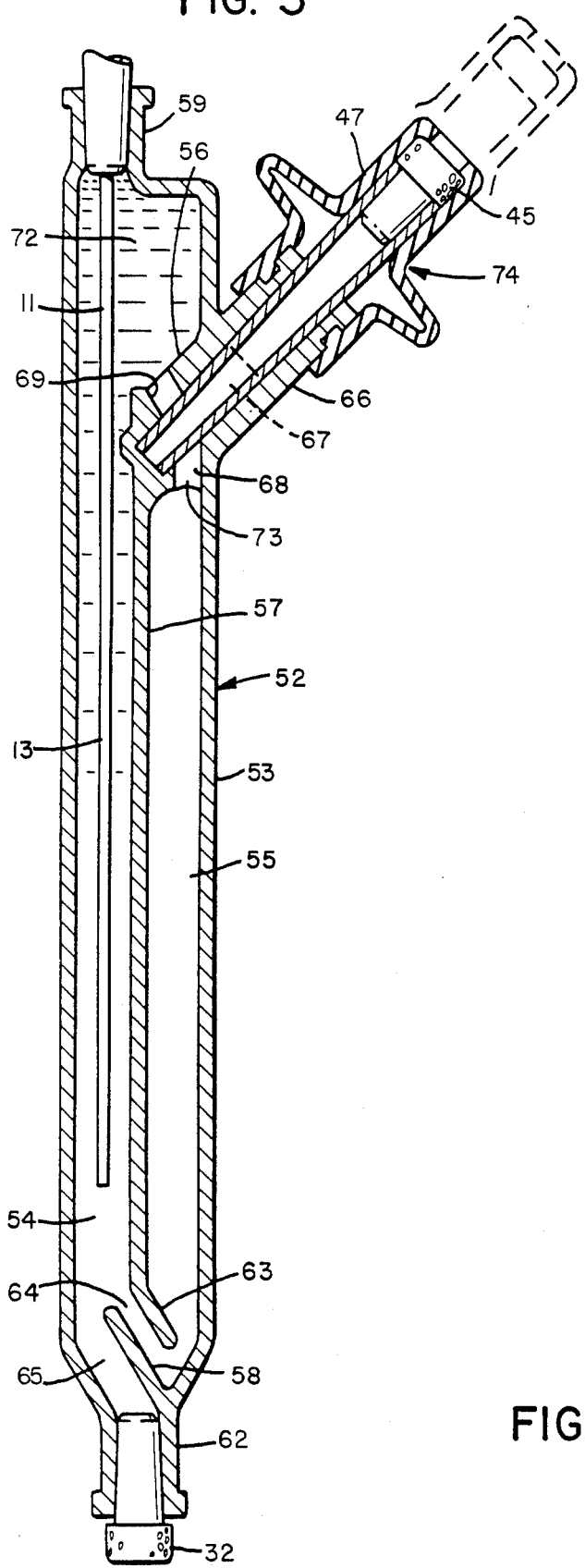
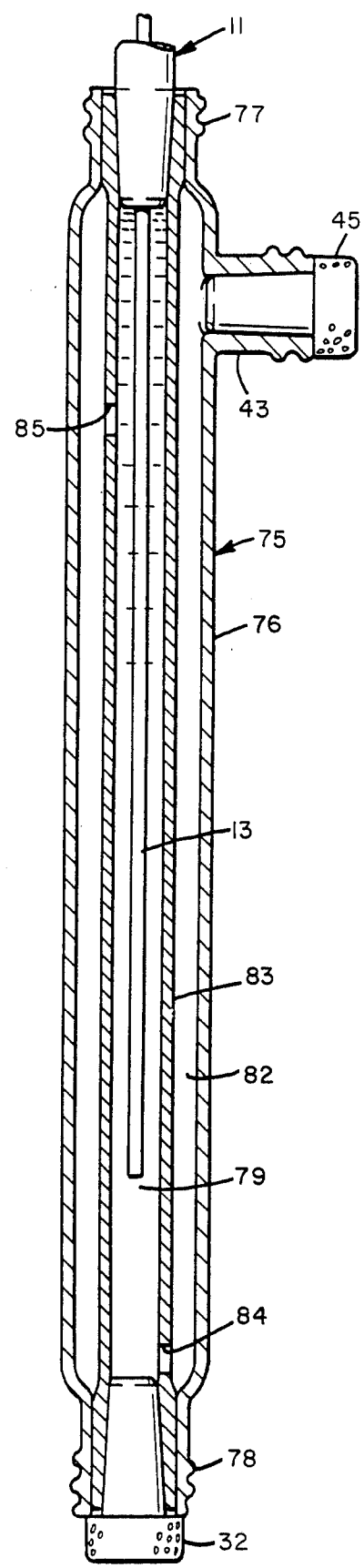

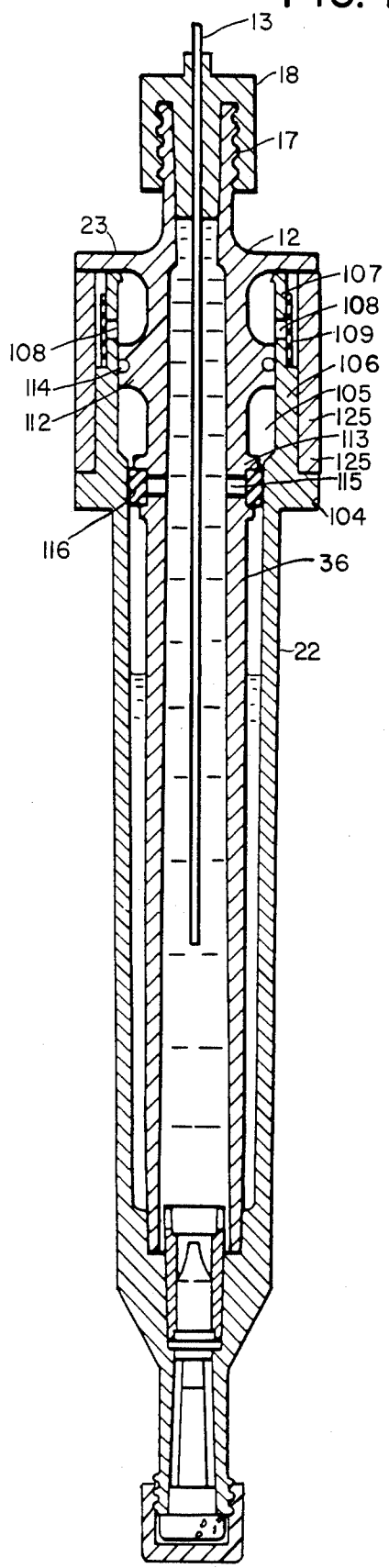
FIG. 7
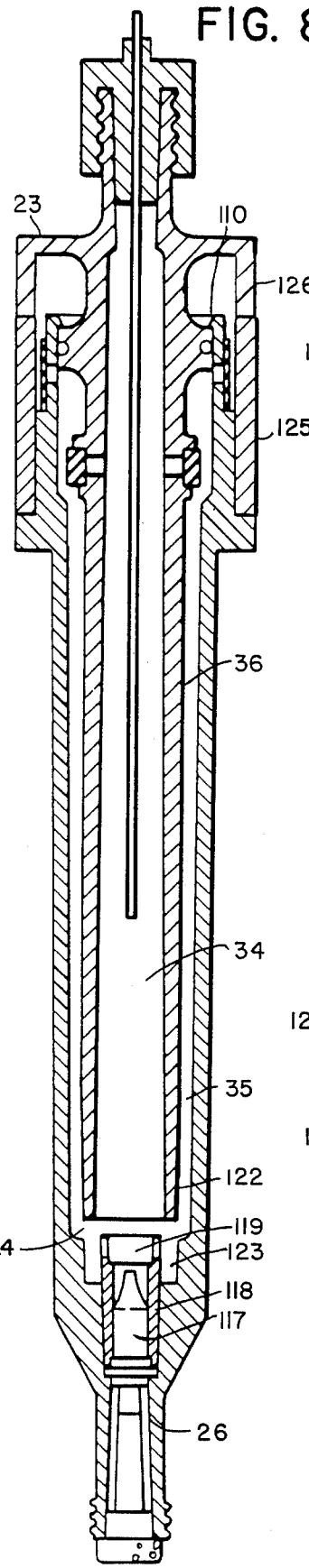
FIG. 8
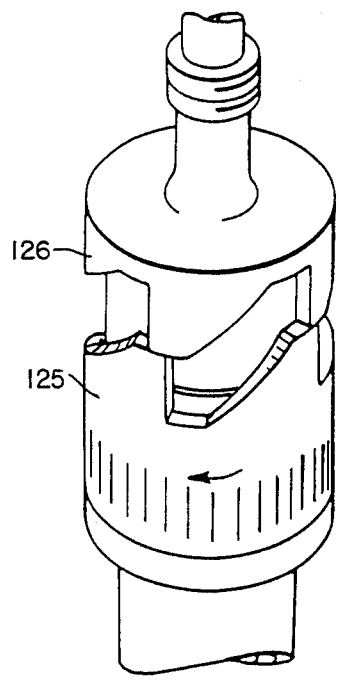
FIG. 9
FIG. 10

APPARATUS FOR CALIBRATING A SENSOR FOR DETECTING THE PRESENCE OF A GAS IN A LIQUID

DESCRIPTION

1. Technical Field

This invention is generally in the field of analytical chemistry devices. More specifically, it is in the field of devices for calibrating sensors that are used to detect the presence of gases in liquids such as blood.

2. Background

Several prior publications and patents describe sensors or probes that include an optical fiber having an end that carries a sensing element, such as a chromophore or a fluorophore, and which is adapted to be placed in contact with a fluid, such as blood, to ascertain the gas content thereof. See, for instance, U.S. Pat. Nos. 4,200,110, 4,476,870, and 4,560,248. The sensing element of the sensor is affected by the presence and/or concentration of gas in the fluid and alters one or more aspects of light transmitted through the fiber in response thereto. For instance, a chromophore may absorb selectively certain wavelengths at certain gas contents or the emitted intensity of light from a fluorophore may be sensitive to gas concentration.

In many of these sensors, the chemistry of the sensing element is such that it is necessary or desirable to keep the sensing element-carrying end of the fiber wet. Further, in all such sensors that are used in vivo for blood gas detection, the sensor end must be sterilized prior to use. A further common requirement of these sensors is that they must be calibrated using buffer liquids of known gas content prior to use. Accordingly, a need exists for a device that will keep the sensors wet prior to use, maintain the sensor in a sterile condition during storage and calibration, and enable rapid and simple calibration by bubbling gas through a calibrating liquid. The present invention provides such a device.

DISCLOSURE OF THE INVENTION

In general terms, the invention is an apparatus for calibrating a sensor that detects the presence or quantity of a gas contained within a liquid comprising:

(a) an elongated calibration chamber adapted to normally hold the sensor in contact with a calibration liquid, the chamber having a calibrating gas inlet through which a calibrating gas may be introduced into the calibration liquid at the lower end of the calibration chamber;

(b) an elongated calibration liquid reservoir chamber adapted to be partly filled with the calibration liquid, the calibration liquid reservoir chamber being situated laterally of the calibration chamber;

(c) at least one calibration liquid passageway interconnecting the calibration chamber and the calibration liquid reservoir chamber in the vicinity of the calibrating gas inlet such that calibrating gas entering the calibration chamber via the inlet aspirates calibration liquid from the calibration liquid reservoir chamber into the calibration chamber via the passageway;

(d) a calibration liquid return and calibration gas outlet passageway interconnecting the calibration chamber and the calibration liquid reservoir chamber at the upper ends thereof through which calibration liquid may be returned to the calibration liquid reservoir chamber and spent calibration gas may exit the calibration chamber; and (e) a spent calibrating gas vent that opens into the upper end of the calibration liquid reservoir chamber above the liquid level therein for removing spent calibrating gas from the apparatus.

The term "laterally" as used to describe the spatial relationship between the calibration chamber and the calibration liquid reservoir chamber is intended to denote a generally parallel, separated relationship that may be achieved by positioning the chambers concentrically or in adjacent parallel planes.

BRIEF DESCRIPTION OF THE DRAWINGS

In the drawings, which are not to scale:

FIG. 3 is an elevational, cross-sectional view of another embodiment of the calibration vial of the invention;

FIG. 4 is an elevational, cross-sectional view of still another embodiment of the calibration vial of the invention;

FIG. 7 is an enlarged elevational sectional view of the preferred embodiment of the calibration vial of the invention showing the vial/sensor assembly as it would be during storage or shipment prior to calibration;

FIG. 8 is an enlarged, elevational view of the calibration vial/sensor assembly of FIG. 7 showing the assembly during the calibration procedure;

FIG. 9 is a perspective view of the upper portion of the calibration vial of FIG. 7 showing the portion in the position depicted in FIG. 7; and FIG. 10 is a perspective view of the upper portion of the calibration vial of FIG. 7 showing the portion in the position depicted in FIG. 8.

In these drawings, like parts are referred to in some instances by the same reference numeral.

MODES FOR CARRYING OUT THE INVENTION

The calibration cuvette or vial of the invention is particularly useful for storing and calibrating blood gas sensors, such as the sensors described in the patents referred to above. These sensors comprise an optical fiber whose tip carries a sensing element, such as a chromophore or fluorophore, or other luminescent moiety which affects a characteristic of light being transmitted back through the fiber in a manner that is related to the level of a particular gas or gases in the blood or other fluid in which the probe is placed in contact.

Figure 1:
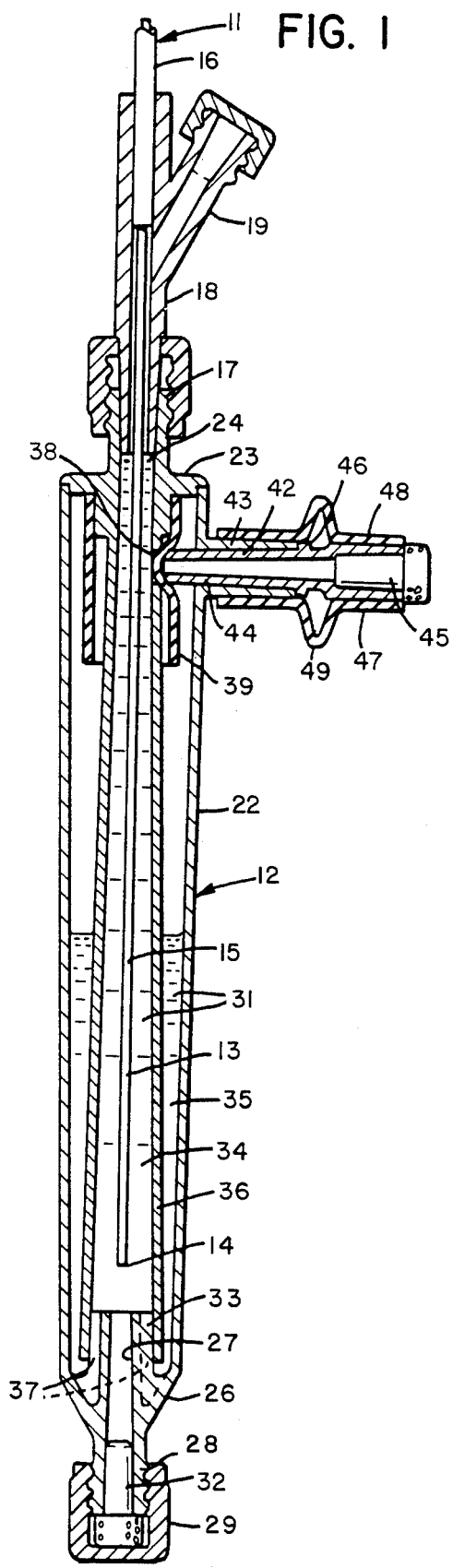
FIG. 1 is an elevational, cross-sectional view of the preferred embodiment of the calibration vial of the invention showing the vial/sensor assembly as it would be during storage or shipment and prior to calibration.

FIG. 1 shows a portion of such a sensor, generally designated 11, contained within a calibration vial, generally designated 12. The sensor includes a light-transmitting optical fiber 13 which carries a sensing element, indicated generally at 14, on the tip of its leading end 15. The segment of the fiber above end 15 is contained within a sheath 16 and is coupled to the threaded upper neck 17 of the vial by a coupler 18. The coupler 18 has a capped hollow sidearm 19 that is used to flush the end of the sensor with fluid during actual use of the sensor.

The vial has an axially elongated generally cylindrical tubular housing 22. The upper end of the housing is closed by an upper end wall 23 having a central bore 24 through which the sensor extends downwardly into the vial. The outer surface of the upper end wall carries the threaded neck 17 and its inner surface carries a boss 25. The lower end of the housing is closed by a generally conical lower end member 26 which has a central bore 27 that serves as an inlet passageway for calibrating gas during the calibration operation. The end member has an exterior threaded neck 28 which is capped with a cap 29 during storage and shipment. The neck serves as a means for coupling the cuvette to a gas source (FIG. 2) in the calibration procedure. The mouth of the neck is plugged with a hydrophobic porous filter element 32 whose pores are sized to permit gas flow but exclude the passage of microorganisms or other contaminants carried by the calibrating gas. The inner side of end member has an upwardly extending boss 33.

The lumen of housing 22 is divided concentrically into an inner calibration chamber 34 in which the optical fiber resides and an outer calibration liquid reservoir chamber 35 by an elongated tubular member 36 that extends axially from boss 25 on the inner side of the upper end wall down to and about boss 33 on the inner side of the lower end wall. The lower end wall has at least one, and preferably from 2 to 6, calibration liquid reflux ports 37 that extend through it and interconnect the chambers 34 and 35. The inlets to the ports are at the lower extremity of the calibration liquid reservoir chamber and their outlets are in boss 33 proximate the inner mouth of bore 27. Alternatively, the ports can be in the inner lower portion of member 36 and the boss 25 can be smooth.

The sidewall of tubular member 36 has an aperture 38 in its upper end near its junction with boss 25. A tubular, open-ended shroud 39 made of an elastomeric material is mounted on boss 25 and extends downwardly therefrom around member 36 to a location below aperture 38. The shroud serves as a means for blocking and closing the aperture during storage and shipment of the assembly and, as discussed below, as a means for preventing spillage of calibration liquid during the calibration procedure. During storage and shipping, the shroud is forced radially inward at the aperture site to sealingly block the aperture by the end of a radially movable hollow plug 42 that is slidably housed within a sidearm 43 that opens through the sidewall of housing 22 opposite the aperture. The plug has a tapered nose 44 and is held in place against the shroud by a friction fit with the inner wall of the sidearm. Its outer end is stoppered with a porous filter 45 of similar structure and function (gas permeable, contaminant impermeable) as filter 32. The nose of the plug has an exterior annular collar 46 that acts in concert with the outer end of the sidearm as a stop to define the inwardmost position of the plug. The size and shape of the inner tip of the plug corresponds in size and shape to the aperture so that the tip is able to hold the shroud against the outer mouth of the aperture in a sealing relationship thereto. An external tubular deformable sheath 47 holds the plug in place within the sidearm when the plug is disengaged from the shroud and withdrawn into the lumen of the sidearm. In this regard, one end of the sheath is mounted fixedly about the the exterior wall of the sidearm and the other end of the sheath is mounted fixedly to a head 48 of the plug which protrudes outwardly from the outer mouth of the sidearm. The portion 49 of the sheath intermediate the fixed ends is able to deform to permit the plug to be moved radially (relative to the housing 22).

Figure 2:
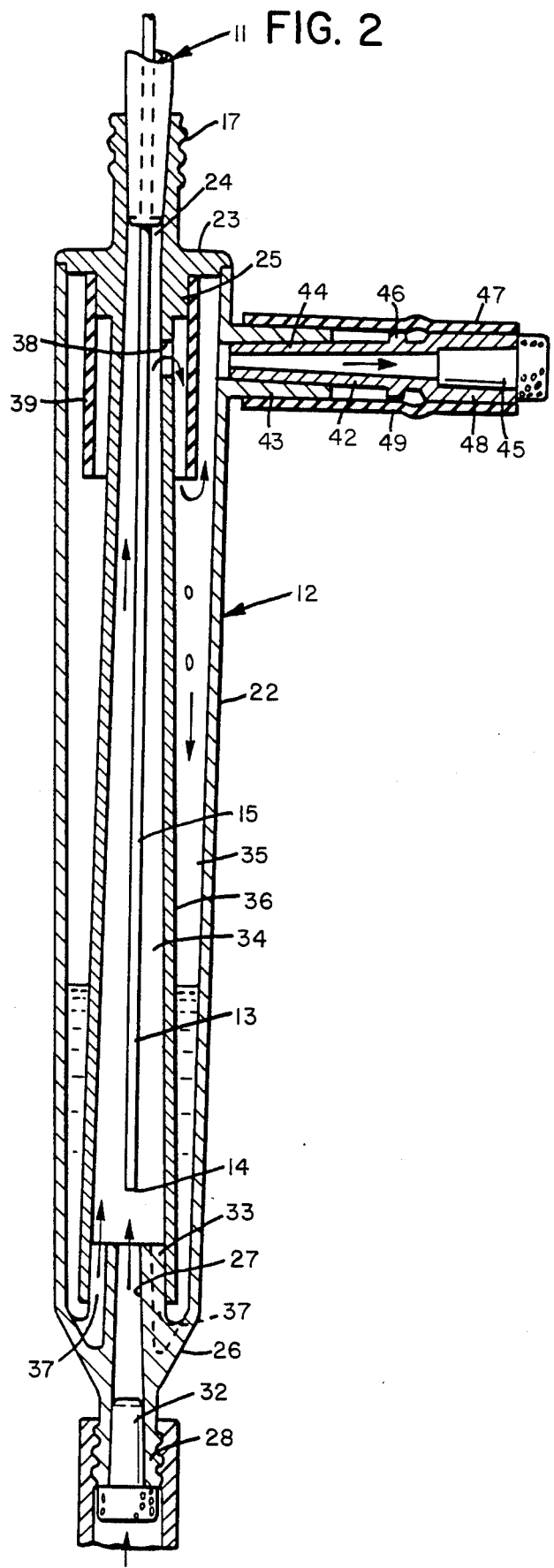
FIG. 2 is an enlarged, elevational, cross-sectional, partly schematic view of the calibration vial/sensor assembly of FIG. 1 showing the assembly during the calibration procedure.
Figure 5:
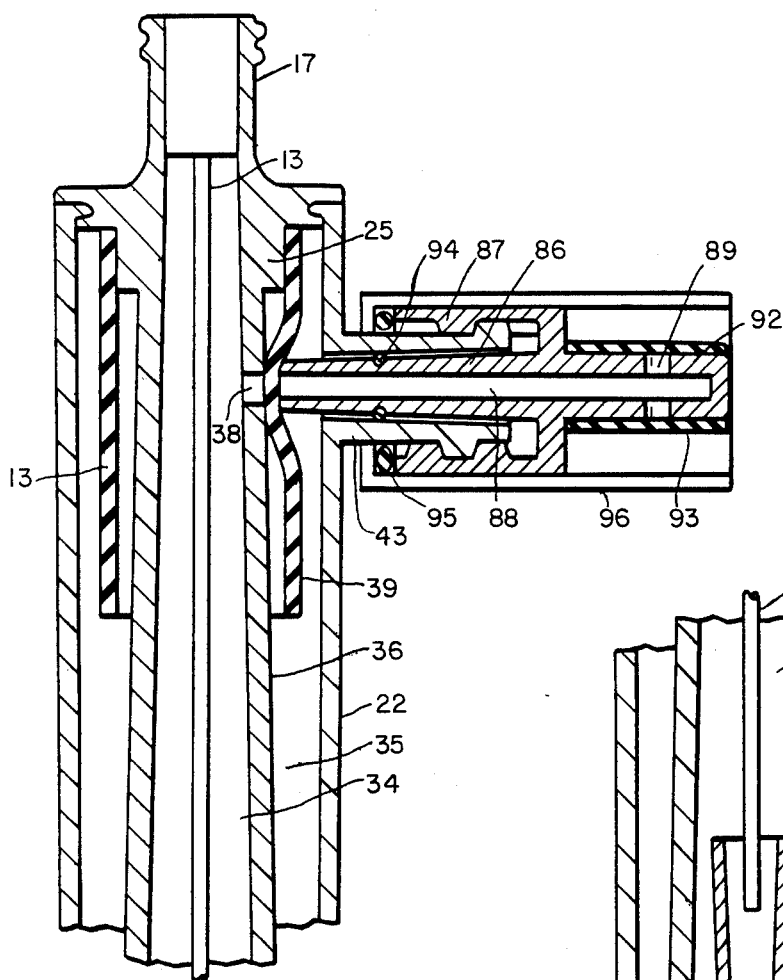
FIG. 5 is an enlarged elevational sectional view of an alternative embodiment of the upper portion of the vial of FIG. 1.

An alternative plug structure to that shown in FIGS. 1 and 2 is illustrated in FIG. 5. In the embodiment of FIG. 5 the sidearm 43 is threaded externally. The radially moveable plug 86 of the embodiment carries a shouldered collar 87 that has internal threads that mate with the exterior threads on the sidearm. The axial bore 88 of the plug does not extend entirely through the plug but is instead intersected by a crossbore 89 at its distal end. The crossbore extends transversely through the head 92 of the plug. An elastomeric sleeve 93 fits about the head 92. The plug is operated by screwing it into and out of engagement with the shroud 13. When the plug is unscrewed so that its tip disengages the shroud, the calibrating gas is free to pass through the plug bore and crossbore. The gas pressure forces the elastomeric sleeve 93 away from the plug head, thus permitting the gas to escape to the atmosphere. The crossbore and sleeve act in concert as a check valve. When not pressurized by escaping gas (i.e., when the plug engages the shroud and seals the aperture to the inner chamber), the sleeve seals the outer mouths of the crossbore and prevents bacterial contamination of the vial. The plug 86 is sealed by means of an internal O-ring 94 and an outer O-ring 95 that is seated between the end of shouldered collar 87 and the inner edge of a tubular plug housing member 96.

The sensor and calibration vial are initially assembled as shown in FIG. 1 with the calibration chamber 34 completely filled and the calibration liquid reservoir chamber 35 partially filled with calibration liquid 31. The blockage of aperture 38 by plug 42 permits the establishment of a pressure differential between the chambers and prevents the liquid levels in the chambers from equilibrating. Once so assembled, the assembly is sterilized by conventional means, such as steam sterilization, and packaged for storage/shipment. The structure of the vial keeps the sensor end 15 fully submersed in liquid despite the attitude at which the assembly is maintained.

Figure 6:
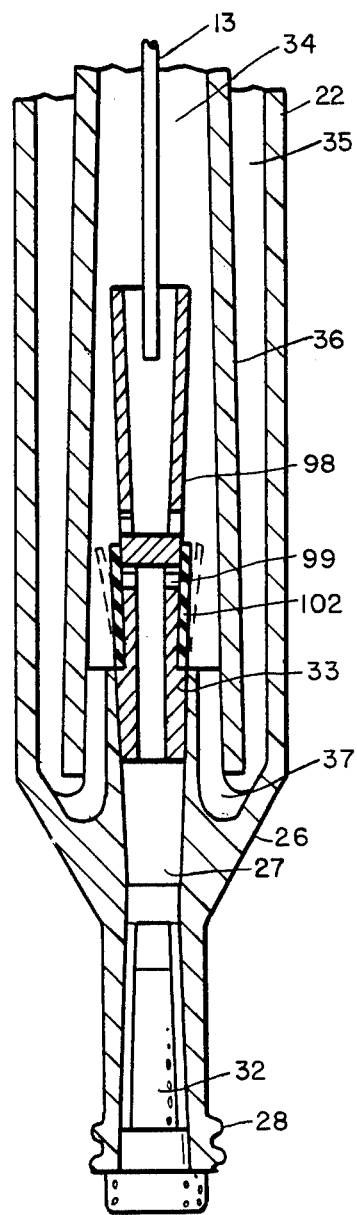
FIG. 6 is an enlarged elevational sectional view of an alternative embodiment of the lower portion of the vial of FIG. 1.

In order to calibrate the sensor, the end cap 29 is removed and the lower end of the vial is connected (as shown in FIG. 2) to a pressure regulated gas source (not shown) by means of the threaded neck 28. The plug 42 is then withdrawn outwardly so that its nose disengages the shroud and is contained wholly within the lumen of the sidearm. As shown in FIG. 2, such withdrawal of the plug permits the elastomeric shroud to relax, whereby the aperture is opened and the shroud is spaced radially from the outer mouth of the aperture. The calibrating gas, which may be a single gas or a mixture of gases (if the sensor is being used to detect gases in blood, the gas will be oxygen, carbon dioxide, nitrogen or a mixture thereof), is then introduced from the gas source into the calibration chamber via bore 27. As indicated previously, any contaminants in the gas will be precluded from entering the vial by filter 32. In FIG. 2 the flow of gas (and calibrating liquid) in the vial during the calibration procedure is depicted schematically by arrows. A Venturi effect is created by the gas entering the bottom of the calibration chamber and calibration liquid is aspirated from the reservoir chamber 35 through the ports 37 upwardly into the calibrating chamber. This effects rapid and efficient mixing of the calibrating gas with the calibrating liquid, thus achieving a predetermined gas partial pressure rapidly in the liquid. FIG. 6 shows an alternative arrangement for introducing calibrating gas into the vial that protects the sensor tip from impinging gas bubbles and reduces noise. In this alternative arrangement, the end of boss 33 is closed and it carries an open-ended tubular baffle 98 that extends upwardly about the end of the sensor. Its sidewall has one or more check valve openings 99 and is enclosed by an elastomeric tube 102. The pressure of the incoming gas forces the elastomeric tube 102 outwardly from the sidewall of the boss (shown in phantom in FIG. 6) thereby permitting the gas bubbles to stream from the check valve holes. The baffle 98 causes the upwardly streaming bubbles to bypass the sensor tip.

The pressure of the incoming gas carries the gas and entrained liquid upwardly in the calibrating chamber until it reaches the aperture 38. The liquid and spent gas exit the calibration chamber via the aperture. The shroud directs them downwardly, thereby preventing the liquid from being spilled or ejected into the sidearm and lumen of the plug and filling the pores of filter 45. The spent gas exits the vial via the sidearm/plug through the filter 45 whereas the entrained liquid (shown as droplets in FIG. 2) falls downwardly in the reservoir chamber 35 to be recycled. The spilling or ejection of liquid into the sidearm/plug is highly undesirable in that blocking the filter pores with liquid will increase substantially the pressure required to drive the calibrating gas through the vial.

The sensor/valve assembly of FIGS. 1, 2, 5 and 6 thus achieves the goals of: (1) keeping the sensor in a sterile, wet condition at all times during storage and shipment regardless of the attitude at which the assembly is positioned, and (2) permitting rapid, sterile circulation of calibrating gas and entrained liquid in the calibrating chamber without spillage of liquid, whereby rapid and accurate calibration of the sensor is achieved.

After the calibration has been completed, the flow of gas through the vial is terminated and the sensor is decoupled and withdrawn from the vial for use. The vial is disconnected from the gas source and discarded.

The alternative sensor/vial assembly shown in FIG. 3 achieves the same goals as that of FIGS. 1 and 2. The principal differences between the vial of FIG. 3 and that of FIG. 1 is in the spatial relationship between the calibration and liquid reservoir chambers and in the structure and manner of closure of the aperture that interconnects those chambers at the upper end of the vial. The vial of FIG. 3 is generally designated 52. It is formed from an elongated housing 53 whose lumen is divided in side-by-side relationship (rather than concentrically as in the cuvette of FIG. 1) into a calibration chamber 54 and a calibration liquid reservoir chamber 55 by internal wall members 56, 57 and 58. The sensor 11 is received into the cuvette through a neck 59 that opens into the calibration chamber. Calibrating gas is introduced into the calibration chamber through a lower neck 62 that is plugged with porous filter 32. The wall 58 and the lower end 63 of wall 57 are spaced and configured to provide a liquid reflux port 64 that interconnects the lower portions of the chambers. Port 64 functions in the same manner as the port(s) 37 of the device of FIG. 1. In this regard its opening into the calibration chamber is positioned proximate the gas inlet passageway 65 to achieve the desired Venturi effect and aspiration of liquid from the reservoir chamber into the calibration chamber by the incoming gas.

Vial 52 has a sidearm 66 at its upper end that depends upwardly from the housing 52 and extends into the interior of the cuvette. The sidearm has a central bore 67 that intersects a generally downwardly depending channel 68 through wall 56. The channel has two segments: one designated 69 that extends between enlarged portion 72 at the upper end of chamber 54 and bore 67 and the other designated 73 that extends longitudinally between the bore and the calibration liquid reservoir chamber. A plug assembly, generally designated 74 and of similar structure to plug 42 of FIG. 1, is slidably seated within the bore. During storage and shipment the plug assembly is in the position shown in solid lines in FIG. 3. During the calibration procedure it is in the position shown in phantom. In its storage position the plug intersects and blocks the channel 68 and prevents liquid from passing from the calibration chamber to the liquid reservoir chamber, with the same effect as the plug/shroud/aperture arrangement of the device of FIG. 1. In its calibration position, the plug assembly is withdrawn into the sidearm and does not block the channel. Calibration liquid is thus free to pass from the calibration chamber to the reservoir chamber via the channel and be aspirated therefrom via port 64 back into the calibration chamber. Correlatively, spent calibration gas is free to pass from the calibration chamber to the atmosphere via segment 69, bore 67, and the central bore and porous filter (or check valve as in FIG. 5) of the plug assembly. Because of the relative attitudes of bore 67 and segment 69 of the channel (they intersect at approximately a right angle), there is no possibility of spillage or ejection of liquid upwardly in the sidearm, and accordingly, no possibility of blocking the pores of the porous filter with liquid.

FIG. 4 depicts an embodiment of the vial which functions essentially the same as the vials of FIGS. 1–3 during calibration. Its structure does not, however, assure that the sensor end will be kept wet during storage/shipment. The cuvette of FIG. 4 is generally designated 75. It has an outer housing 76, and upper neck 77 through which the sensor assembly is received, a lower neck 78, and a porous filter-plugged sidearm at its upper end through which spent calibration gas is vented to the atmosphere. The lumen of its housing is divided concentrically into a calibration chamber 79 and a calibration liquid reservoir chamber 82 by an elongated centrally positioned tube 83. The ends of the tube are enlarged and respectively fit tightly into the necks 77 and 78. The sensor assembly is received in the upper end of the tube and the lower end of the tube is plugged with a hydrophobic porous filter. Calibration gas is introduced into the chamber 79 through the hydrophobic porous filter at the lower end of the tube. The central tube has two apertures in it: one, designated 84, located just above the enlarged bottom end of the tube and the other, designated 85, located near the upper end of the tube at a location that does not face the inner mouth of the sidearm. These apertures interconnect the two chambers, with the lower aperture functioning as a liquid reflux port similarly to the reflux ports 37 and 64 of the other depicted embodiments and the upper aperture operating as apertures 38 and channel 68 of the other embodiments for venting spent calibrating gas and returning calibration liquid from the calibration chamber to the liquid reservoir chamber during the calibration operation. Since there is no means for blocking the upper aperture, the levels of liquid in the two chambers will equilibrate during storage and shipment. Accordingly, depending upon the particular attitude in which the assembly is placed, the sensor tip may not be submersed. It will, of course, be submersed if the assembly is maintained in a vertical position. The relative positions of the upper aperture and the mouth of the sidearm (i.e., they do not face each other) make it impossible for liquid to be spilled or ejected into the sidearm during the calibration operation.

FIGS. 7-10 show an alternative and preferred embodiment of the calibration vial. This embodiment achieves all of the goals and functions of the vials of FIGS. 1, 2, 5 and 6 and, in addition, is easier to manufacture and manipulate from its storage configuration (FIG. 7) to its use configuration (FIG. 8).

As seen in FIGS. 7-10, the structure of the upper portion of the vial, which includes the calibration liquid and calibration gas outlet passageway and the spent calibrating gas vent, is substantially different from the structure shown in the preceding figures. Instead of using a plug assembly as shown in FIGS. 1, 2, 5, and 6 the vial of FIGS. 7 to 10 operates on the principle of a cam-actuated spool valve. The cylindrical housing 22 of the vial of FIG. 7 has an outwardly extending annular shoulder 104. The portion 105 of the lumen of the housing above the shoulder has a larger diameter than the portion of the lumen below the shoulder. The lumen portion 105 is defined by the segment 106 of the housing that extends upwardly from shoulder 104. Segment 106 has an integral upper, subsegment 107 of smaller outer diameter which has a one or more radial apertures 108 that serve as spent calibrating gas vents. The outer openings of apertures 108 are covered by an elastomeric sleeve 109 that functions in the same manner as sleeve 93 of the embodiment shown in FIG. 5. Thus, apertures 108 and sleeve 109 act in concert as check valves, during the calibration procedure to release spent calibrating gas from the vial. As shown in FIG. 7, the upper edge of segment 107 is seated against the inner side of end wall 23 in the storage/shipment configuration. The upper edge of segment 107 carries an inwardly extending tang 110 that acts as a stop and engages the edge of boss 112 in the calibration configuration (FIG. 8).

The upper portion of the generally tubular member 36 that extends downwardly from the inner side of end wall 23 of the vial of FIGS. 7-10 has two outwardly extending annular bosses 112 and 113. The outer edge of boss 112 engages the inner side of segment 106 and carries and O-ring 114 that forms a seal with the inner side of segment 106. As seen in FIGS. 7 and 8, O-ring 114 is seated below apertures 108 in the storage/shipment configuration and above apertures 108 in the calibration configuration. The other boss 113 defines the outer opening(s) of one or more bores 115 that extend radially through member 36 and serve as the calibrating liquid return and calibration gas outlet passageway(s). The outer edge of boss 113 is slotted and carries an elastomeric shroud 116 in the slot that functions in the same manner as shroud 39 of the embodiments of FIGS. 1, 2 and 5. Shroud 116 is compressed between the inner side of housing 22 and boss 113 in the storage/shipment configuration and is disengaged from housing 22 and relaxed in the calibration configuration.

The structure of the lower end of the calibration vial of FIGS. 7 and 8 through which the calibrating gas enters the vial is also different from that of the vial of FIGS. 1, 2 and 6. The upper end of bore 26 is fitted with a check valve 117. A sleeve 118 fits in the bore and about the check valve and a porous body 119 that acts as a gas diffuser is seated in the upper end of the sleeve 118. The sidewall of member 36 is tapered at 122 so that it is able to form a leur taper seal in the storage/shipment configuration when it is seated about sleeve 118 and against the walls of a recess 123 in the inner side of endwall 26 of the vial. As shown in FIG. 8, when the vial is in its calibration configuration, the tip of member 36 is withdrawn upwardly out of the recess to open annular passageway 124 between the calibration chamber 34 and the calibration liquid reservoir chamber 35. This structure permits the calibration liquid reservoir chamber to be sealed from the calibration chamber when the vial is in its storage/shipment configuration. Such structure provides the additional advantage that buffers of different properties may be stored in the calibration chamber and calibration liquid reservoir chamber prior to calibration and then mixed when the vial is manipulated to its calibration configuration. Thus, it is possible to have the calibration chamber charged with a first liquid whose properties (e.g., pH, ionic strength) are ideal for storage and the liquid reservoir charged with a second liquid whose properties and volume are such that when mixed with the first liquid provide a mixture that is ideal for calibration.

The procedure for charging the two chambers with different liquids would be to fill the vial in its calibration configuration with the second liquid, manipulate the vial to its storage/shipment position to seal the chambers off from each other, aspirate the second liquid from the calibration chamber and refill the calibration chamber with the first liquid. When the vial is manipulated back to the calibration configuration, passageway 124 is opened and the two liquids are free to mix.

The means by which the vial is manipulated between the configurations shown in FIGS. 7 and 8 is an activating ring 125. Its cam-like operation is illustrated in FIGS. 9 and 10. The bottom edge of the ring is flat and slidingly seats against the upper edge of shoulder 104. Its upper edge is serrated and interfits with a fixed ring-like cam follower member 126 that extends downwardly from the edge of endwall 23. As shown, cam 126 has serrations that complement the serrations of ring 125. Ring 125 is rotatable (indicated by the arrow in FIG. 10) and acts as a cam when it is rotated. Upon rotation, the action of the cam (sloping edges of the serrations of ring 125) on the follower drives the follower and hence the endwall 23 and tubular member 36 upwardly from the storage position shown in FIGS. 7 and 9 to the calibration position shown in FIGS. 8 and 10. As indicated previously, this manipulation has the effects of (1) moving the O-ring 114 from below to above the spent calibration gas vent(s), thereby opening the vent(s) to the calibration liquid reservoir chamber on the inside of the vial and the atmosphere on the outside of the vial, (2) moving the shroud 116 out of engagement with housing 22, thereby permitting the calibration liquid return and calibration gas outlet passageway to be opened, and (3) moving the tapered end of member 36 out of sealing engagement with recess 123, thereby opening passageway 124 between the calibration and calibration liquid reservoir chambers.

In all other respects the calibration vial of FIGS. 7-10 operates in essentially the same manner as the vials of FIGS. 1, 2 and 5, 6.

Modifications of the above described modes for carrying out the invention that are obvious to those of skill in the fields of mechanical engineering, analytical chemistry device design, and related fields are intended to be within the scope of the following claims.

I claim:

1. An apparatus for calibrating a sensor that detects the presence or quantity of a gas contained within a liquid comprising:
   (a) an elongated calibration chamber adapted to hold the sensor in contact with a calibration liquid, the chamber having a calibrating gas inlet through which a calibrating gas may be introduced into the calibration liquid at the lower end of the calibration chamber;
   (b) an elongated calibration liquid reservoir chamber adapted to be partly filled with the calibration liquid, the calibration liquid reservoir chamber being situated laterally of the calibration chamber;
   (c) at least one calibration liquid passageway interconnecting the calibration chamber and the calibration liquid reservoir chamber in the vicinity of the calibrating gas inlet such that calibrating gas entering the calibration chamber via the inlet aspirates calibration liquid from the calibration liquid reservoir chamber into the calibration chamber via the passageway;
   (d) a calibration liquid return and calibrating gas outlet passageway interconnecting the calibration chamber and the calibration liquid reservoir chamber at the upper ends thereof through which calibration liquid may be returned to the calibration liquid reservoir chamber and spent calibrating gas may exit the calibration chamber; and
   (e) a spent calibrating gas vent that opens into the upper end of the calibration liquid reservoir chamber above the liquid level therein for exhausting spent calibrating gas from the apparatus.

2. The apparatus of claim 1 wherein the gas is nitrogen, oxygen or carbon dioxide, the liquid is blood, and the apparatus is also for storing the sensor under sterile conditions.

3. The apparatus of claim 2 wherein the sensor includes an optical fiber having an end that carries a sensing element that must be kept wet, said end being the portion of the sensor that is held in contact with the calibration liquid.

4. The apparatus of claim 3 including means for opening and closing the calibration liquid return and calibrating gas outlet passageway, whereby said passageway may be closed for storing the sensor and opened for calibrating the sensor.

5. The apparatus of claim 3 including means for opening and closing the calibration liquid passageway, whereby said calibration liquid passageway may be closed for storing the sensor and opened for calibrating the sensor.

6. The apparatus of claim 5 wherein the calibration liquid passageway is closed during storage, thereby sealing the calibration chamber from the calibration liquid reservoir chamber, the calibration chamber is charged with a first liquid whose properties are suitable for storing the sensor, and the calibration liquid reservoir is charged with a second liquid which, when mixed with the first liquid, provides the calibration liquid.

7. The apparatus of claim 3 wherein the lower end of the calibration chamber is situated in a side-by-side relationship to the calibration liquid reservoir chamber and the upper end of the calibration chamber extends above the calibration liquid reservoir chamber and the apparatus includes means for opening and closing the calibration liquid return and calibrating gas outlet passageway, whereby said passageway may be closed for storing the sensor and opened for calibrating the sensor.

8. The apparatus of claim 7 wherein the vent depends upwardly and intersects said passageway and said means is a hollow plug received in the vent that is movable therein between a first position in which the plug blocks the passageway and a second position in which the plug does not block the passageway.

9. The apparatus of claim 3 including means for opening and closing the spent calibrating gas vent whereby the vent may be closed to the calibration liquid reservoir for storing the sensor and opened to the calibration liquid reservoir for calibrating the sensor.

10. The apparatus of claim 3 wherein the calibration chamber and calibration liquid reservoir chamber are generally cylindrical and are situated concentrically with the calibration chamber being situated inwardly of the calibration liquid reservoir chamber.

11. The apparatus of claim 10 including means for opening and closing the calibration liquid return and calibrating gas outlet passageway, whereby said passageway may be closed for storing the sensor and opened for calibrating the sensor.

12. The apparatus of claim 11 wherein said vent and said calibration liquid return and calibrating gas outlet passageway face each other and the means for opening and closing the calibration liquid return and calibrating gas outlet passageway comprises an elastomeric shroud interposed between said vent and said passageway and a hollow plug received in said vent that is movable between a first position in which the plug contacts the shroud and biases the shroud against the passageway to sealingly close the passageway and a second position in which the plug does not contact the shroud and bias it so as to close the passageway.

13. The apparatus of claim 12 wherein the shroud prevents liquid from being spilled from said passageway into said vent when said plug is in the second position.

14. The apparatus of claim 10 including means for opening and closing the calibration liquid passageway, whereby said calibration liquid passageway may be closed for storing the sensor and opened for calibrating the sensor.

15. The apparatus of claim 10 including means for opening and closing the spent calibrating gas vent whereby the vent may be closed to the calibration liquid reservoir for storing the sensor and opened to the calibration liquid reservoir for calibrating the sensor.

16. The apparatus of claim 1 wherein the calibration chamber and calibration liquid reservoir chamber are generally cylindrical and are situated concentrically with the calibration chamber being situated inwardly of the calibration liquid reservoir chamber.

17. The apparatus of claim 16 wherein the apparatus includes separate means for
   (i) opening and closing the calibration liquid return and calibrating gas outlet passageway,
   (ii) opening and closing the calibration liquid passageway; and
   (iii) opening and closing the spent calibrating gas vent.

whereby said passageways vent may be closed for storing the sensor and opened for calibrating the sensors.

18. The apparatus of claim 17 wherein said separate means includes means for moving the calibration chamber and calibration liquid reservoir chamber axially relative to each other.

19. The apparatus of claim 18 wherein the calibration chamber and calibration liquid reservoir chamber are defined by a tubular outer housing having two closed ends and an inner tubular member having one open end that fits concentrically within the housing, with the calibration chamber being the lumen of the inner tubular member and the calibration liquid chamber being the space between the housing and the inner tubular member, the calibration liquid return and calibrating gas outlet passageway being one or more apertures in the tubular member, the spent calibrating gas vent being one or more apertures in the housing, and the calibration liquid passageway being defined by the space between the open end of the inner tubular member and an end of the housing and said separate means includes a rotable cam member mounted about the housing, a cam follower affixed to the inner tubular member, said follower being moved axially from a first position to a second position by rotation of the cam member, a seal member on the tubular member which forms a seal between the tubular member and the housing below the spent calibration gas outlet in said first position whereby the spent calibration gas vent is closed to the calibration liquid reservoir chamber and is located above the spent calibration gas outlet in said second position whereby the spent calibration gas vent is opened to the calibration liquid reservoir, and an elastomeric shroud on the tubular member that covers the calibrating liquid return and calibrating gas outlet passageway and is compressed by the housing in said first position whereby the calibrating liquid return and calibrating gas outlet passageway is closed and is spaced from the housing in the second position, whereby the shroud is relaxed and the calibrating liquid return and calibrating gas outlet passageway is opened.

20. The apparatus of claim 16 wherein there are a plurality of spaced calibration liquid passageways.

21. The apparatus of claim 20 wherein there are two to six spaced calibration liquid passageways.

22. The apparatus of claim 16 wherein the calibrating gas inlet and the spent calibrating gas vent each has a hydrophobic filter means that permits the passage of gas but prevents the passage of contaminants into the apparatus.

23. The apparatus of claim 22 including means for preventing calibration liquid from being spilled into said vent.

24. The apparatus of claim 1 including means for preventing calibration liquid from being spilled into said vent.

25. The apparatus of claim 1 wherein the calibrating gas inlet and the spent calibrating gas vent each has a filter means that permits the passage of gas but prevents the passage of contaminants into the apparatus.

26. The apparatus of claim 1 wherein the relative positions of the vent and the calibration liquid return and calibrating gas outlet passageway are such as to preclude spillage of calibrating liquid from the passageway into the vent.

27. The apparatus of claim 1 wherein the calibration chamber and calibration liquid reservoir chamber are situated in a planar, side-by-side relationship.

* * * * *